United States Patent [19]

Haas

[11] Patent Number: 4,684,666

[45] Date of Patent: Aug. 4, 1987

[54] STABILIZED LIQUID ANALGESIC COMPOSITIONS

[75] Inventor: Ronald T. Haas, Robbinsville, N.J.

[73] Assignee: Haas Pharmaceuticals, Inc., Robbinsville, N.J.

[21] Appl. No.: 897,803

[22] Filed: Aug. 19, 1986

[51] Int. Cl.$^4$ .............................................. A61K 31/19
[52] U.S. Cl. ................................................... 514/557
[58] Field of Search ........................................ 514/557

[56] References Cited

U.S. PATENT DOCUMENTS 3,385,886 5/1968 Nicholsen .......................... 514/957
4,447,451 5/1984 Mueller .............................. 514/557

OTHER PUBLICATIONS

Chem. Abst., 103-76147v, (1985).

*Primary Examiner*—Stanley J. Friedman
*Attorney, Agent, or Firm*—Niblack & Niblack

[57] ABSTRACT

A stabilized liquid ibuprofen syrup suitable for oral administration comprising: from 50 to 400 mg of ibuprofen per 5 ml of syrup; said ibuprofen suspended in an aqueous liquid having more than 50% by weight of a pharmaceutically acceptable polyhydric alcohol bodying agent; a sweetening agent; and a pH of higher than 7.0 and below 7.7.

11 Claims, No Drawings

STABILIZED LIQUID ANALGESIC COMPOSITIONS

FIELD OF INVENTION

This invention relates to medicinal orally administrable stabilized liquid analgesic compositions, and more specifically relates to stabilized liquid analgesic compositions having ibuprofen (p-isobutylhydratropic acid) as their active ingredient. These compositions, which have the form of moderately viscous syrups, are useful for the treatment of pain, inflammatory conditions and other conditions including adult respiratory distress syndrome.

Ibuprofen is a non-steroidal anti-inflammatory drug widely used in the treatment of minor pain and degenerative and rheumatic diseases of the joints. Despite its wide use in several classes of patients, and its suitability for administration to pediatric and geriatric patients who frequently can not take solid oral dosage forms such as tablets and capsules, the industry has not been successful in developing stable, elegant and palatable preparations. Because of ibuprofen's low water solubility, unpleasant bitter taste and lack of stability in water, previous preparations displayed the problems of chemical and visual instability, resulting in products of short storage life. Thus, pediatric and geriatric patients, and others who can not, for a variety of reasons, swallow tablets or capsules, have been limited to liquid acetaminophen products for the relief of pain. While acetaminophen is a widely used analgesic and anti-pyretic agent, it lacks anti-inflammatory activity and is not as an effective pain reliever as ibuprofen.

PRIOR ART

Nicholson et al, U.S. Pat. No. 3,385,886, discloses liquid suspensions and mixtures of ibuprofen containing chloroform water, with and without orange flavor, and an unsweetened elixir containing ethanol and glycerol. These products have limited shelf life, poor flavor and substantial turbidity, not to mention the unsuitability of chloroform-containing liquid products for administration to infants, small children and elderly patients.

Mueller, U.S. Pat. No. 4,447,451, exemplifies an oral suspension containing 80 mg of ibuprofen aluminum salt per ml consisting of about 96% sucrose and 1.4% other inactive ingredients dissolved in water. This suspension rapidly develops cloudiness and is not chemically stable for long periods.

Moore et al report a clinical trial using a liquid ibuprofen product, International Journal of Clinical Pharmacology, Therapy and Toxicology, Vol. 23 No 11-1985 (pp 573–577). While the Moore suspension formulation is not disclosed in the body of the paper, a footnote reveals that it was compounded by the assignee of the Mueller patent and was 400% more concentrated than that of the patent on an active ingredient basis.

Despite the well-recognized efficacy of ibuprofen, and its wide use, there remains a long standing need for a suitable liquid oral dosage form of this valuable drug which is not only stable, but is especially suitable for administration to pediatric and geriatic patients. The present invention fulfills that need.

DETAILED DESCRIPTION OF THE INVENTION

The liquid compositions of this invention are aqueous ibuprofen-containing syrups containing from 50 to 400 mg of ibuprofen per 5 ml of syrup and comprising: a therapeutically effective amount of ibuprofen or a pharmaceutically acceptable salt or ester thereof; more than 50% by weight water compatible bodying agent; less than 1% stabilizers; an alkalinizing agent in an amount suitable to provide a final composition pH of above 7.0 and preferably between 7.0 and 7.7, most preferably 7.3 to 7.5; a sweetening agent; and a pharmaceutically acceptable antioxidant.

The stabilized liquid ibuprofen formulations of this invention include both sucrose sweetened and sugar free formulations suitable for administration to diabetics and other patients whose sugar intake should be restricted. Because of the bitter and unpleasant flavor of ibuprofen, it is desirable to have a product of high sweetness.

The term "water compatible bodying agent" means a pharmaceutically acceptable water miscible or dissolvable material that yields a water-clear aqueous suspension or solution of increased viscosity.

The term "stabilizer" as used in this specification means a material having dispersing, suspending or hydrophilic emulsifying properties that does not substantially modify clarity or viscosity of water solutions at low levels; and is capable of forming a particulate or molecular film which surrounds ibuprofen molecules.

"Alkalinizing agent" means a pharmaceutically acceptable hydroxide compound capable of rendering the final syrup above pH 7.0.

"Sweetening agent" as used herein means nutritive and non-nutritive sweeteners that are pharmaceutically acceptable and are stable in aqueous solution.

The term "antioxidant" means a pharmaceutically acceptable water soluble antioxidant stable at alkaline pH.

An important aspect of this invention is the inclusion of a major portion of water compatible material or materials that contribute to a rather heavy and uniform viscosity in the final composition. Suitable materials must be capable of being freely incorporated into water without affecting clarity of the resultant suspension or solution, and not have pronounced or undesirable affect upon the flavor of the product. Pharmaceutically acceptable polyhydric alcohols are highly useful as bodying agents because of their solvent and miscibility properties, contribution to viscosity and generally pleasant taste. Those that are preferred include glycerol, sorbitol, mannitol and propylene glycols. Particularly suitable components include sorbitol and glycerol. These should be incorporated at a level of from about 50% to 75% by weight of the final composition. An especially preferred combination is the use of 1 part of glycerol to about 3 to 4 parts of sorbitol.

It is permissible to use other materials such as sucrose as an incidental part of the bodying agent component but such inclusions should not constitute a major part thereof because of the general metabolic undesirability of including larger amounts of sugar and the visual haze that develops in the syrup from its use unless special precautions are taken. While there has been no recognition by the prior art, the use of high levels of sucrose, both cane and beet, results in shortened stability of the ibuprofen liquid products by reason of haze formation when usual commercial sugar products are added. If sucrose is incorporated in any quantity, and the maximum should be less than 40%, it is essential that high purity sugar such as Bottler's Grade Extra Fine, No Floc, sold by Holly Sugar be used in order to minimize haze development in storage.

Stabilizing agents provide protection for the ibuprofen active medicament by shielding it from other components, as well as aiding mixing during processing. While they are employed at very low levels, less than 1% by weight of the total syrup, they provide multiple very useful functions by first aiding in dispersing and suspending the ibuprofen particles and then forming a protective molecular or fine particle coat around the suspended drug in the final product.

Several classes of compounds suitably serve this function, especially hydrophilic emulsifying agents and colloidal clays. Natural emulsifiers of plant and animal origin are not preferred because they are susceptible to discoloration and precipitation under storage conditions. These include gelatin, lecithin, tragacanth and acacia. Finely dispersed solids such as colloidal clays are highly preferred. These include bentonite, aluminum silicate, colloidal magnesium aluminum silicate such as Veegum brand supplied by Vanderbilt. Another particularly preferred stabilizing agent is the synthetic polymer, polyvinylpyrrolidone (PVP).

Optimally, a combination of stabilizing ingredients is included. One such combination is 1 part of PVP to 2 parts of colloidal magnesium aluminum silicate. These are included in a total amount of from 0.25% to 1.0% by weight. Particularly preferred is a blend of 0.11% PVP to 0.22% Veegum. It is not necessary and is undesirable to employ amounts over 1.0% because of possible slight turbidity that may result under adverse storage conditions.

It is essential to the optimum stability of the final product that the pH be maintained in the alkaline range at all times. An acceptable range is above 7.0 and below 7.7, although best results are achieved at a pH of 7.3 to 7.5. In order to maintain this level, an alkalizing agent such as a hydroxide must be used. Suitable compounds include potassium hydroxide and sodium hydroxide. While other hydroxides are useful they are not preferred. For example, while calcium hydroxide is a pharmaceutically acceptable material, and its solutions exhibit strong alkalinity, reaction between it and air causes production of haze and formation of calcium carbonate precipitate which renders the syrup undesirable for long term storage unless air is excluded. Because of the unpleasant taste characteristics of ibuprofen which are enhanced by being placed in suspension, it is most desirable to mask its natural flavor with sweetness.

Because of the stability problems encountered with sucrose, coupled with the general undesirability of using a metabolizable sugar in most patients, the preferred sweetener is sodium saccharin. While other sweeteners may be used, water stability is necessary for products expected to have an extended shelf life. Aspartame is suitable from the organoleptic standpoint but decomposes in water solution over an extended time period, making it less desirable.

A further necessary aspect of this invention is the protection of the product from entrapped air which results in oxidation and lessened stability. An antioxidant which is water soluble and suitable for inclusion in an oral drug preparation should be included. While compounds such as ascorbic acid derivatives such as ascorbyl palmitate may be employed, they are not preferred because of their acidic nature and generally lower solubilities. The preferred antioxidant is sodium metabisulfite because of its effective scavenging of oxygen incorporated within the product during manufacture or later contacting the product. The acceptable range of antioxidant is from about 0.10% to 0.25%, with 0.18% optimally being used.

Viscosity of the product should be controlled for optimum stability. A viscosity of about 1000 to 3000 centipoise at 20° C., as measured by the Brookfield Synchro-Lectric viscometer, is the preferred range. Finished product of somewhat less thickness are capable of being stored for commercially acceptable time periods, but these are less able to withstand adverse conditions which may be encountered in storage and shipment.

In addition to the necessary components of the compositions, many desirable ingredients may be added. These include flavoring, colorings, alcohol and other preservatives such as parabens. Ethanol, included at a level of about 12% to 25%, and preferably about 15% to 20%, serves as both a microbial inhibiting preservative and a mixing aid of benefit during processing of the product. Butyl paraben, at about 0.014% coupled with propyl paraben at a lower level approaching its limit of solubility, about 0.008%, together inhibit an extended range of organisms.

Fruit flavors such as cherry and citrus, which have a slight bitter component to their flavor profile, are most suitable.

During compounding and processing of the compositions, it is very desirable to minimize or exclude air. Observing this precaution assists in obtaining a better quality product of satisfactory shelf life.

The following examples are illustrative of the invention and are not intended to be limiting.

EXAMPLE I

A 1,000 gallon batch of aqueous syrup for oral use, containing 200 mg of ibuprofen per 5 ml, one teaspoon, dose is prepared from the following:

| | |
|---|---|
| Ibuprofen (micronized) | 151 kg |
| Sorbitol | 2322 kg |
| Glycerol | 710 kg |
| Ethanol (95%) | 800 kg |
| Veegum | 10 kg |
| PVP | 5 kg |
| Sodium metabisulfite | 8 kg |
| Sodium hydroxide | 21 kg |
| Carmine solution* | 61 kg |
| Wild cherry flavor (Cosomo #37) | 7 kg |
| Sodium saccharin | 20 kg |
| Butyl paraben | 0.65 kg |
| Propyl paraben | 0.36 kg |
| Deionized water, q.s. | 1000 gal |

The Carmine solution is prepared from the following ingredients:

| | |
|---|---|
| Propylene glyol USP | 28468 gm |
| Carmine No. 40 Powder | 4058 gm |
| Sodium Hydroxide Pellets | 1395 gm |
| Hydrochloric acid | 3246 gm |
| Deionized water, q.s. | 67133 gm |

Separate solutions of the Veegum, PVP and sodium hydroxide are prepared by dissolving each in water and cooling to 25°-30° C. About 800 kg of water is added to a mixing tank and ibuprofen is dissolved, followed by the addition of sodium hydroxide solution until a pH of 7.3 to 7.5 is reached. The glycerol is added to the tank which is heated to 85° C. and sorbitol, the parabens and saccharin are added. The metabisulfite is dissolved in twice its weight of water and added to the batch which has been cooled to 25° C. With constant mixing the PVP and the Veegum solutions are incorporated. The carmine solution is added and after mixing the ibuprofen solution is placed in the compounding tank, followed by the cherry flavoring. The batch is purged with nitrogen, followed by homogenization and deaeration by passage through an Oakes mixer and a Versator.

EXAMPLE II

Following the procedure of Example I, a stable syrup containing 100 mg of ibuprofen alumimum salt per 5 ml is prepared from the following ingredients:

| Ingredient | Amount (Kg) |
| --- | --- |
| Ibuprofen, aluminum salt | 7.57 |
| Sorbitol | 160.00 |
| Propylene glycol | 80.00 |
| Ethanol (95%) | 80.00 |
| Veegum | 1.00 |
| PVP | 0.50 |
| Sucrose (Holly Extrafine) | 113.00 |
| Sodium metabisulfite | 0.80 |
| Potassium hydroxide | 2.37 |
| Carmine solution | 6.10 |
| Citrus lemon peel flavor | 0.66 |
| Butyl paraben | 0.065 |
| Propyl paraben | 0.033 |
| Deionized water, q.s. | 100 gal |

EXAMPLE 3

Following the process of Example I, a syrup containing 400 mg ibuprofen per 5 ml is provided from the following ingredients:

| Ingredient | Amount (Kg) |
| --- | --- |
| Ibuprofen | 30.28 |
| Sorbitol | 160.00 |
| Glycerine | 95.00 |
| Ethanol 190 proof | 75.00 |
| Bentonite | 1.00 |
| PVP | 0.50 |
| Sodium saccharin | 2.00 |
| Sodium metabisulfite | 0.80 |
| Sodium hydroxide | 2.00 |
| Carmine solution | 6.10 |
| Lemon oil flavor | 0.66 |
| Butyl paraben | 0.068 |
| Propyl paraben | 0.036 |
| Deionized water, q.s. | 100 gal |

EXAMPLE IV

Following the process of Example I, a syrup containing 50 mg ibuprofen per 5 ml is provided from the following ingredients:

| Ingredient | Amount (Kg) |
| --- | --- |
| Ibuprofen | 3.78 |
| Veegum | 10.00 |
| PVP | 5.00 |

-continued

| Ingredient | Amount (Kg) |
| --- | --- |
| Sodium hydroxide | 21.00 |
| Alcohol USP 190 proof | 80.00 |
| Glycerine | 70.00 |
| Sodium metabisulfite | 0.80 |
| Carmine solution | 6.10 |
| Wild cherry flavor | 0.66 |
| Butyl paraben | 0.065 |
| Propyl paraben | 0.035 |
| Calcium saccharine | 20.00 |
| Sorbitol | 218.00 |
| Deionized water, q.s. | 100 gal |

The above description has been given by way of illustration. It will be understood by those skilled in the art that modifications may be made without departing from the spirit and the scope of the claimed invention.

The invention claimed is:

1. A stabilized ibuprofen-containing syrup containing from 50 to 400 mg of ibuprofen per 5 ml of syrup and comprising: a therapeutically effective amount of ibuprofen or a pharmaceutically acceptable salt or ester thereof; from 50 to 75% by weight of a water compatible bodying agent; less than 1% by weight of a stabilizer adapted to form a particulate or molecular film about the ibuprofen particles; an alkalinizing agent in an amount suitable to provide a final composition of alkaline pH of from above 7.0 to 7.7; sufficient sweetening agent to render the syrup sweet; and from about 0.10 to 0.25% by weight of a pharmaceutically acceptable antioxidant.

2. The stabilized ibuprofen liquid formulation of claim 1 wherein the pH of the final composition is between 7.3 and 7.5 inclusive.

3. The stabilized ibuprofen liquid formulation of claim 2 wherein said sweetening agent is extrafine, no floc sugar.

4. The stabilized ibuprofen liquid formulation of claim 1 wherein said sweetening agent is sodium saccharin.

5. The stabilized ibuprofen liquid formulation of claim 1 wherein said bodying agent is a polyhydric alcohol bodying agent.

6. A stabilized liquid ibuprofen syrup containing from 50 to 400 mg of ibuprofen per 5 ml of syrup comprising: from 40 to 50 weight percent of sorbitol; from 0.05 to 0.25 weight percent of polyvinylpyrrolidone; from 0.15 to 0.5 weight percent colloidal clay; sodium saccharine in an amount to render the syrup sweet; from 0.1 to 0.25 weight percent sodium metabisulfite; and a therapeutically effective amount of ibuprofen or a pharmaceutically acceptable salt or ester thereof, said syrup having a pH of from 7.3 to 7.5, inclusive.

7. A stabilized liquid ibuprofen syrup suitable for oral administration comprising: from 50 to 400 mg of ibuprofen per 5 ml of syrup; said ibuprofen suspended in an aqueous liquid having more than 50% by weight of a pharmaceutically acceptable polyhydric alcohol bodying agent; a sweetening agent; and a pH of from 7.0 to 7.7.

8. The stabilized liquid ibuprofen syrup of claim 7 wherein said pH is 7.3 to 7.5 inclusive.

9. The syrup of claim 1 wherein the viscosity is about 1000 to 3000 centipoise at 20° C.

10. The syrup of claim 6 wherein the viscosity is about 1000 to 3000 centipoise at 20° C.

11. The syrup of claim 7 wherein the viscosity is about 100 to 3000 centipoise at 20° C.

* * * * *